US00PP12189P2

(12) United States Plant Patent
Karniel

(10) Patent No.: US PP12,189 P2
(45) Date of Patent: Nov. 6, 2001

(54) TABLE SEEDLESS GRAPE PLANT NAMED 'AUTUMN GIANT'

(76) Inventor: Shachar Karniel, 48 Nili Boulevard, Zichron Yackov (IL)

( * ) Notice: Subject to any disclaimer, the term of this patent is extended or adjusted under 35 U.S.C. 154(b) by 0 days.

(21) Appl. No.: 09/419,529

(22) Filed: Oct. 18, 1999

(51) Int. Cl.[7] ..... A01H 5/00

(52) U.S. Cl. ..... Plt./207

(58) Field of Search ..... Plt./207

*Primary Examiner*—Bruce R. Campell
*Assistant Examiner*—June Hwu
(74) *Attorney, Agent, or Firm*—Christie, Parker & Hale, LLP

(57) ABSTRACT

Described is a new grape variety that produces substantially uniform, large white table grapes on a productive plant.

3 Drawing Sheets

BACKGROUND OF THE INVENTION

The invention relates to a new and distinct variety of the *Vitis vinifera* species which produces white seedless table grapes.

The new variety is the result of an induced mutation ("embryo rescue process") of the variety "*Kishmish Moldavski*". The new variety has been asexually reproduced by micropropagation (tissue culture) in Cesena, Italy.

SUMMARY OF THE INVENTION

The new variety 'Atumn Giant' is a large, white seedless table grape with large production, e.g. about 40 to 60 bunches per vine, with an average of about two bunches per shoot.

Asexual reproduction by micropropagation of the new variety as performed in Cesena, Italy and Zichron Yackov, Israel, shows that the foregoing and other distinguishing characteristics come true to form and are established and transmitted through succeeding propagations.

BRIEF DESCRIPTION OF ILLUSTRATIONS

The accompanying illustrations shows typical specimens of the vegatative growth and berries of the new variety grown on own roots depicted in color as nearly true as it is reasonably possible to make the same in a color illustration of this character.

DESCRIPTION OF THE NEW VARIETY

Figure 1:
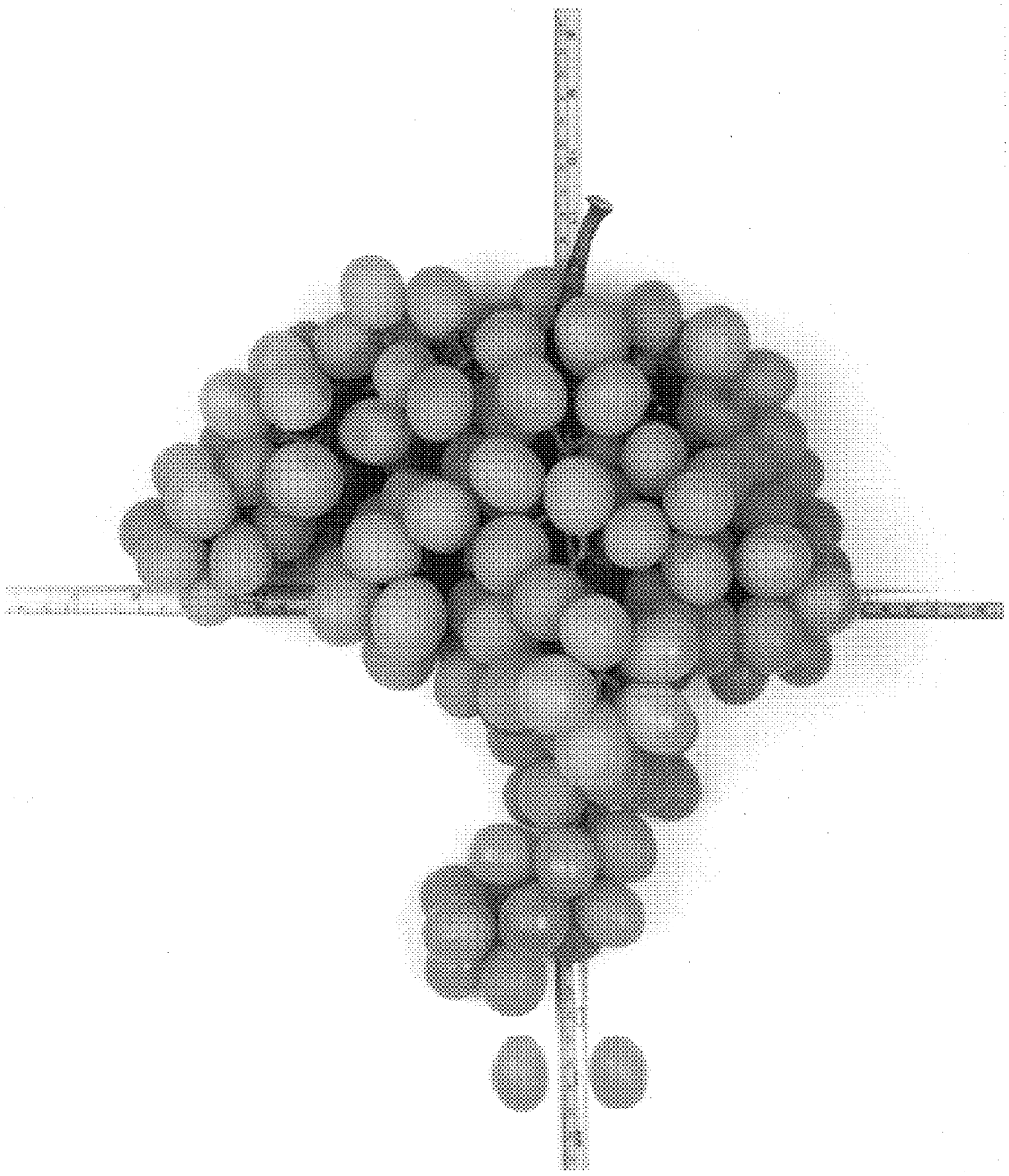
FIG. 1 is a bunch of grapes.
Figure 2:
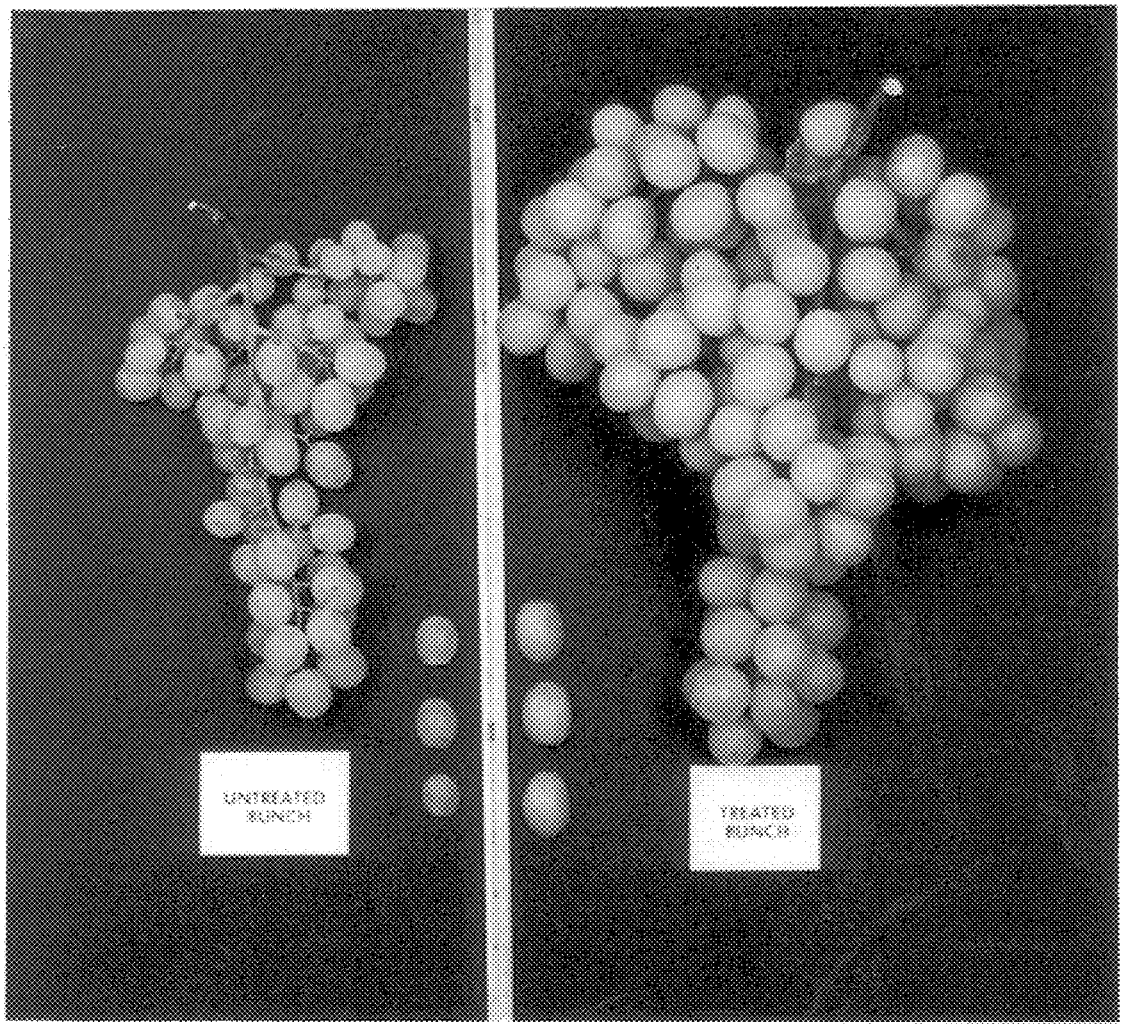
FIG. 2 is an illustration of grapes of the new variety treated with Gibberellic acid (on right) and untreated.
Figure 3:
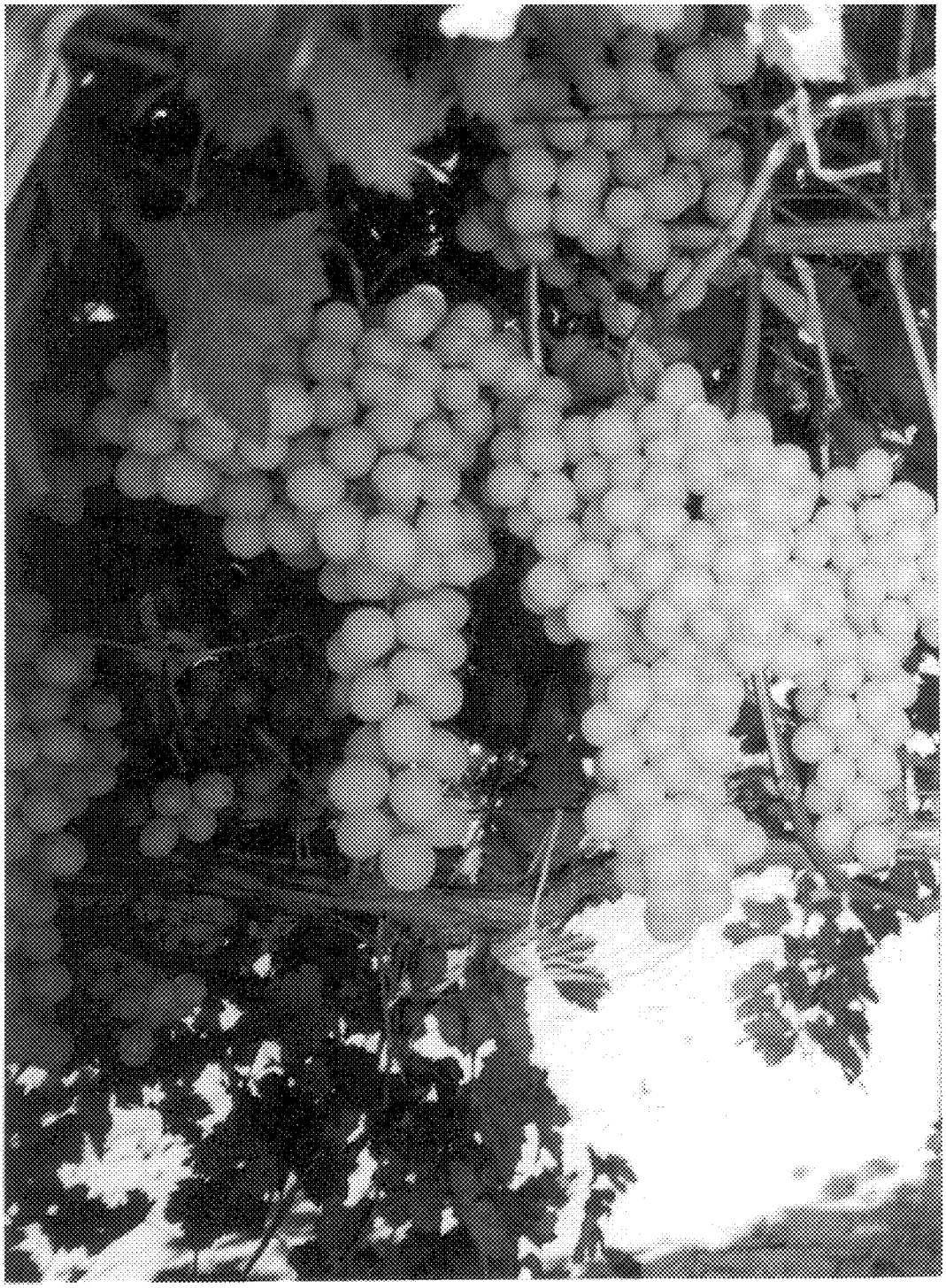
FIG. 3 is an illustration of grapes as grown on a vine.

The following is a detailed description of a three year old specimens of the new variety grown outdoors on own roots in Zichron Yackov, Israel, in April to September. The color terminology used is in accordance with the Dictionary of Colors, by Maerz and Paul, first Edition, 1930. Phenotypic expression may vary depending on environmental, climate and cultural conditions.

Vine:

*Size.*—Medium spread canopy with medium leaf size.

*Form.*—Semi-drooping, i.e. more upright than drooping.

*Vigor.*—Moderate to strong vigor.

*Time of sprouting.*—In Israel about March 28$^{th}$ to 30$^{th}$.

*Productivity.*—Heavy production, average 40 to 60 branches per vine, 2 bunches per shoot. When the vine crop is limited to single cordon "V" shape, each side of the vine carries 7×2 buds at each spur, for a total of 14 spurs, and when green pruning practice is applied and only 2 shoots per spur and 1 bunch per shoot remain, there are a total of 28 shoots per vine formation. In this case the total amount of bunches carried by the vine will be about 28 bunches per vine, and each bunch will be 1½ lbs., yielding about 2 boxes per vine and a total of about 1,100 boxes per acre. This number is considered to be high production crop. The shoot length reaches about 12'. However, if this variety is grown on double cordon (quarto cordon) in "V" shape trellising, the total number of spurs per vine will increase the crop yield up about 1,600 boxes per acre. The heave load on the vine will reduce shoot length to about 9' each.

Trunk:

*Size.*—Medium.

*Surface structure.*—The vine canopy is dense and the shoots have short joints which produce more leaves per square feet, and short laterals of about 3 to 5 leaves. These together develop a high density canopy surface, which is a unique characteristic of the new variety along with vine — the large amount of short laterals covering the vine surface.

*Diameter.*—About 1¼"; Surface diameter in a single cordon "T" trellising planting space of about 12' by 7' with the canopy cover of about 105 square feet. Three year old vines grown in own roots in sandy loamy soil carry produce about 28 bunches with an average weight of about 1½ lbs., the color of the vine is near greenish with yellowish background near 24-L-1. The 4$^{th}$ year plants on own roots in sandy loamy soil with the trunk raised above soil level are about 4', and the diameter of about 1¼" about 1' above ground level.

*Bark.*—Bark surface of 3 year old vines is smooth with no bark swelling, structure is solid firm longitudinal veins near 55-J-12. The bottom part is selected for observation because the color of the upper part color is directly influenced by direct sun, dust, age and humidity, which may be variable while the lower part is always protected by the upper part and observations are therefore more constant.

Canes:

*Size.*—Mature cane about ½" wide; average mature cane length about 9' to 12'.

*Number.*—In the third growing year, there are about 14 spurs; 28 shoots (canes) per vine.

*Diameter.*—About ½" for shoots with a bunch; about ⅝ inches for shoots without a bunch.

*Color.*—Own root vine, mature third year cane surface is relatively smooth with deep reddish brown color, near 13-B-7.

*Form.*—Straight, upright. Nodes: Width of nodes at center of canes having a bunch is about ½"; width of canes without a bunch is about ⅝". Internodes: Width of nodes at center is about ⅜" with bunch; about 7/16" without bunch; length about 4½" with bunch; about 5¼" without bunch. There is a cane width difference that correlates with the yield. When the crop vine carrying is less, the thickness of the cane increases and vice versa. The difference in node thickness is related to the cane thickness, that is the reason two different widths are described for a heavy crop, and for a light crop. The node measurement is taken at the center of the node, thus, the size differences. Canes that carry a bunch are about ⅜" to ½" thick and canes not carrying a bunch are about ⅝" thick.

*Tendrils.*—Number: In the early stage, spring tendrils are large and upright; at maturity tendrils break off at the splitting point, very few remain on the mature cane. The number of tendrils per cane changes during the growing season. In order to be more specific, the flowering stage as a parameter of tendrils per shoot; the number of tendrils per shoots is between 5 and 7 according to the development and the position of the shoot in the vine.

*Color.*—As tendril development is actually equivalent to every growth part of the vine and aging as well, we can identify the stages of growing by the color at each stage; when the tendril base before the splitting point becomes mature and the second stage of the tendril occurs the coloration of the mature base of the tendril includes reddish strips on the lower part of the tendril up to the splitting point near 53-B-1, while the basic part of the tendril is fully mature a green color above the split point indicates young in age and is near 21-K-3. Tendril thickness: About 1/16" to 1/18". Tendril length: About 10¼" to 7½". Tendril form: V-shaped with no curlicue in the end. Tendril texture: Slightly firm, not woody, the tendril starts from green and changes to dormancy; both color and firmness change, some tendrils the age at harvest time are woody and have about 3 to 4 loops on the support wire, in this stage of harvest, the new variety tendril is slightly firm, but not woody.

Flowers:

*Type.*—Male and female fully developed; stamens taller than pistils which make the flower self-fertile. Flower quantity averages about 200 flowers per bunch.

*Color.*—The general color of the flower is white creamy near 10-A-1; stamen color — yellow cream — Naples yellow near 10-A-2; Pedicel color — light yellow/green near 15-G-6.

*Date of bloom.*—First bloom April 20 in hot valleys of Northern hemisphere; last bloom May 5 in hot valley of Northern hemisphere.

*Average size.*—Typical of species.

*Pedicel.*—Length: About ⅛". Color: Near 10-A1.

*Stamen.*—Length: About ⅛". Color: Near 10-A-2.

Foliage:

*Leaves.*—Unlike other common varieties because the new variety has lateral growth from every node about the fruit, about 6–10 joints with no tendrils; laterals increase the density of the foliage. Length: Mature leaf about 5⅛"; immature leaf about 4". Width: Mature leaf about 6 13/16"; immature leaf about 3¾". Thickness: Density (average number of leaves above each cluster) up to about 25 leaves.

*Color.*—Veins: Upper surface near 20-K-2; Lower surface near 20-C-1. Lower surface: Mature leaf near 23-L-3; immature leaf near 23-L-3. Upper surface: Mature leaf near 24-L-1; immature leaf near 24-L-1.

*Texture.*—Lower surface: Leaf texture smooth and shiny on immature leaves. Upper surface: Fairly smooth, no hairs. Number of lobes: 3 main lobes with 2 sub lobes on sides. Terminal lobe form: Very deep oval lobes compared with leaf general size. Petiolar Color: Near 53-B-1. Sinus depth of Petiolar: Between 1½" up to 1¾" depending on location and vine strength. Sinus shape: Slightly open — Sinus does not appear larger than the petiole Shape is a mixture of both straight sides and both convex sides. Shoot tip: Half open, green with red stripes. Shoot: Upright with half open top, three or more tendrils, round, green color with reddish stripes. Leaf blade: Serrated about 1/16" to 5/16" in depth with two indentations about ½" to ⅝".

Fruit: (1) Period A — from ve'raison (beginning of fruit ripening) the berries are deep green and round; (2) Period B — at maturity fruit treated with gibberellic acid are extremely large and round, crunchy and meaty with mild flavor, low sugar and low acid; the eating quality is good, meaty and juicy as well; the berries are well attached; the variety has very little shatter.

*Average size of berry.*—Treated with gibberellic acid large berry about 1 3/16" to 1 1/18", untreated about ⅞" to 1".

*Average berry weight.*—Treated with gibberellic acid about 11.34 g.; not treated about 4.5 g.

*Sugar/acid ratio.*—Treated with gibberellic acid about 15 to 16 brix.; not treated about 17 to 18 brix.

*Set of berry.*—The variety has very little shatter.

*Thickness of skin.*—Variable from shaded fruit to exposed fruit; shaded fruit thickness slightly more than 'Thompson seedless' (unpatented).

*Color of skin.*—Creamy bright yellowish color near 11-H-6 (untreated); 11-H-4 (treated).

*Color of pulp.*—Translucent.

*Texture of berry pulp.*—Meaty and juicy.

*Presence of seeds.*—Seed trace at maturity light green almost invisible but when fruit is held on the vine beyond maturity or kept in cold storage they turn to brown and are about 1/16".

*Ripening date.*—First week of September in hot growing regions of Northern hemisphere.

*Storage quality.*—Excellent in color, up to about 90 days in storage, eating quality and shape keep well.

*Shipping quality.*—No shatter, no discoloration, no affect on flavor, no shriveling.

Cluster: Bunch has conical shape as grown; weight about 2 lbs.

*Size.*—Bunch length is about 12" to 18" and average width is about 9" to 12.5"; strong main stem; no abscission point; stem color at maturity on mature canes is yellowish cream except the peduncle is 50% brown (mature color); about 1 to 2" long and about 3/16" to 1/4" thick.

*Berry size uniformity.*—Very uniform in the bunch and from bunch to bunch; no second crop bunches. Cluster Shape: Mostly conical; long bunch with medium to short shoulders, treated bunch with gibberellic acid is solid and not flexible. Peduncle Length: Short. Thickness: Thick. Pedicel Length: Short/thick.

Use: For table grapes.

Uniqueness:

*Size.*—Large white seedless grape in this time frame of maturity.

*Ripening time.*—First week of September.

*Productivity.*—Average about 40 to 60 bunches per vine, stable productivity.

*Resistance to fruit rotting.*—Good.

*Storage capacity.*—Excellent storing life with no decadence.

Disease resistance: Same as most of common varieties in Spain.

I claim:

1. A new and distinct white seedless grape plant known as 'Autumn Giant' substantially as shown and described.

* * * * *